(12) United States Patent
Koda et al.

(10) Patent No.: US 10,315,217 B2
(45) Date of Patent: Jun. 11, 2019

(54) METHOD FOR MANUFACTURING ELASTIC TUBULAR BODY

(71) Applicant: KANEKA CORPORATION, Osaka-shi, Osaka (JP)

(72) Inventors: Takuro Koda, Settsu (JP); Katsuyuki Tsuneoka, Settsu (JP)

(73) Assignee: KANEKA CORPORATION, Osaka-Shi (JP)

( * ) Notice: Subject to any disclaimer, the term of this patent is extended or adjusted under 35 U.S.C. 154(b) by 235 days.

(21) Appl. No.: 15/317,575

(22) PCT Filed: May 20, 2015

(86) PCT No.: PCT/JP2015/064516
§ 371 (c)(1),
(2) Date: Dec. 9, 2016

(87) PCT Pub. No.: WO2015/194307
PCT Pub. Date: Dec. 23, 2015

(65) Prior Publication Data
US 2017/0100741 A1 Apr. 13, 2017

(30) Foreign Application Priority Data
Jun. 18, 2014 (JP) .................................. 2014-125753

(51) Int. Cl.
*B05D 1/04* (2006.01)
*B05D 7/02* (2006.01)
(Continued)

(52) U.S. Cl.
CPC ........... *B05D 1/04* (2013.01); *A61M 25/0009* (2013.01); *B05B 5/08* (2013.01); *B05D 1/045* (2013.01); *B05D 7/02* (2013.01); *B05D 2254/02* (2013.01)

(58) Field of Classification Search
CPC .. B05D 1/045; B05D 1/04; B05B 5/00; B05B 5/087
(Continued)

(56) References Cited

U.S. PATENT DOCUMENTS 3,933,965 A * 1/1976 Gallone ................. B43K 1/003
264/177.15
4,377,603 A * 3/1983 Itoh ......................... B05B 5/032
118/627
(Continued)

FOREIGN PATENT DOCUMENTS

JP 60-38049 A 2/1985
JP 2000-153217 A 6/2000
(Continued)

OTHER PUBLICATIONS

International Search Report, issued in PCT/JP2015/064516, PCT/ISA/210, dated Aug. 18, 2015.
(Continued)

*Primary Examiner* — Cachet I Sellman
(74) *Attorney, Agent, or Firm* — Birch, Stewart, Kolasch & Birch, LLP

(57) ABSTRACT

A method for manufacturing an elastic tubular body, comprises a first step of inserting a rod-like conductive member 2 into an elastic tubular body 1; a second step of giving a first electrical potential to the rod-like conductive member 2; and a third step of applying a coating material 31 charged to a second electrical potential to the elastic tubular body 1; wherein the rod-like conductive member 2 has a deformed cross-sectional shape in a direction vertical to an axial direction.

13 Claims, 5 Drawing Sheets

(51) Int. Cl.
*B05B 5/08* (2006.01)
*A61M 25/00* (2006.01)

(58) Field of Classification Search
USPC .......................... 118/621, 626; 427/2.1–2.31
See application file for complete search history.

(56) References Cited

U.S. PATENT DOCUMENTS

| | | | | |
|---|---|---|---|---|
| 5,071,593 | A * | 12/1991 | Takahashi | B05D 1/045 252/500 |
| 5,618,589 | A * | 4/1997 | McFarland | B05B 5/14 118/308 |
| 5,824,403 | A * | 10/1998 | Eidenschink | B05D 1/045 428/300.4 |
| 6,030,371 | A * | 2/2000 | Pursley | A61M 25/0009 427/195 |
| 6,399,206 | B1 * | 6/2002 | Carswell | B05D 1/045 428/423.1 |
| 6,669,980 | B2 * | 12/2003 | Hansen | A61L 2/08 427/2.1 |
| 7,553,377 | B1 * | 6/2009 | Chen | B05B 5/08 118/500 |
| 7,892,592 | B1 * | 2/2011 | Chen | B05B 13/0228 118/500 |
| 7,985,440 | B2 * | 7/2011 | Pacetti | A61F 2/91 118/232 |
| 7,988,934 | B2 * | 8/2011 | Balmer | G01N 35/0099 422/501 |
| 8,092,864 | B2 * | 1/2012 | Isch | A61F 2/88 427/2.24 |
| 8,187,661 | B2 * | 5/2012 | Madriaga | B05B 13/0228 118/320 |
| 8,465,607 | B1 * | 6/2013 | Kelley | F02K 9/18 149/87 |
| 8,881,675 | B2 * | 11/2014 | Plans | A61F 2/82 118/500 |
| 2003/0029347 | A1 * | 2/2003 | Lloyd | F42B 12/32 102/489 |
| 2003/0185964 | A1 * | 10/2003 | Weber | A61L 27/34 427/2.25 |
| 2005/0131513 | A1 * | 6/2005 | Myers | A61F 2/958 623/1.11 |
| 2006/0216431 | A1 * | 9/2006 | Kerrigan | B05B 5/087 427/458 |
| 2007/0077435 | A1 * | 4/2007 | Schachter | A61L 27/34 428/411.1 |
| 2008/0113084 | A1 | 5/2008 | Myers | |
| 2009/0214756 | A1 * | 8/2009 | Chen | B05B 5/08 427/2.25 |
| 2009/0285974 | A1 * | 11/2009 | Kerrigan | A61L 31/14 427/2.21 |
| 2010/0256746 | A1 * | 10/2010 | Taylor | A61K 31/435 623/1.42 |
| 2011/0022027 | A1 * | 1/2011 | Morishita | A61L 29/085 604/509 |
| 2012/0064141 | A1 * | 3/2012 | Andreacchi | B05D 3/144 424/422 |
| 2013/0345795 | A1 * | 12/2013 | Fox | A61F 2/06 623/1.44 |
| 2016/0067032 | A1 * | 3/2016 | Soletti | A61F 2/06 427/2.25 |
| 2017/0021384 | A1 * | 1/2017 | Nabeshima | B05D 1/045 |

FOREIGN PATENT DOCUMENTS

| | | |
|---|---|---|
| JP | 2000-153218 A | 6/2000 |
| JP | 2007-534362 A | 11/2007 |
| JP | 2008-534155 A | 8/2008 |

OTHER PUBLICATIONS

Written Opinion of the International Searching Authority, issued in PCT/JP2015/064516, PCT/ISA/237, dated Aug. 18, 2015.

* cited by examiner

[FIG. 1A]
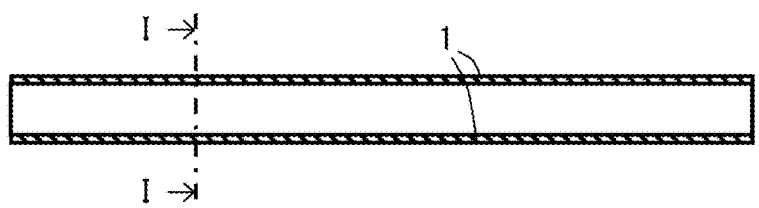
[FIG. 1B]
[FIG. 1C]
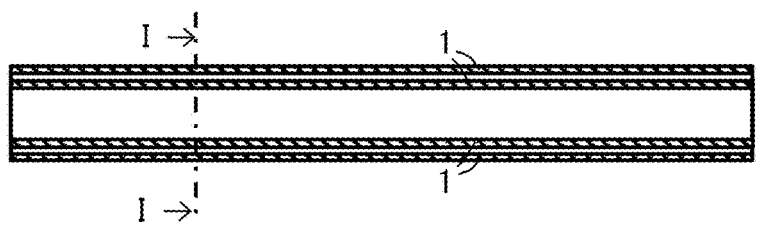
[FIG. 1D]
[FIG. 1E]
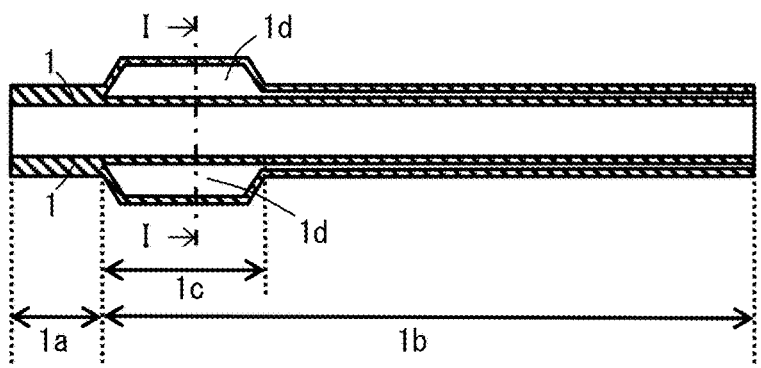
[FIG. 1F]
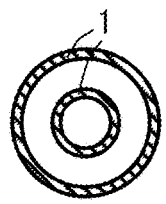

[FIG. 2]
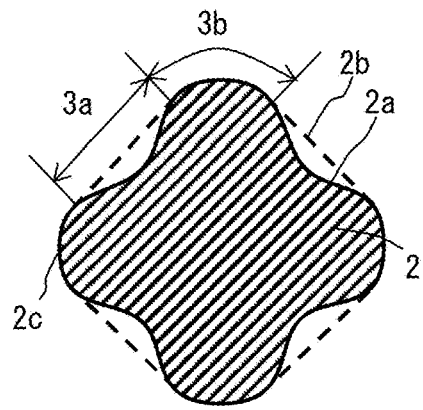
[FIG. 3]
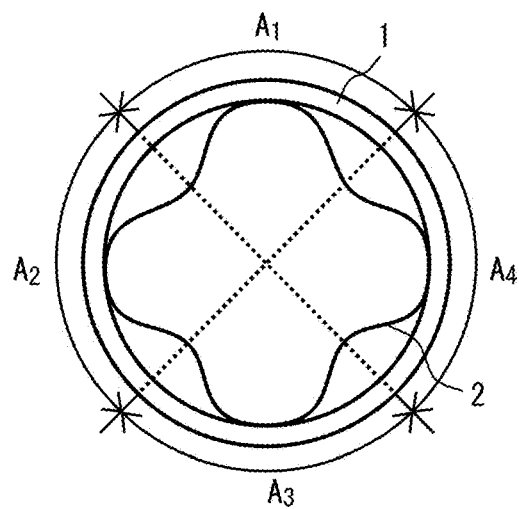
[FIG. 4]
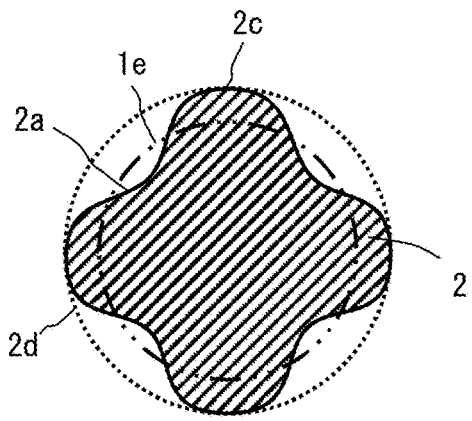

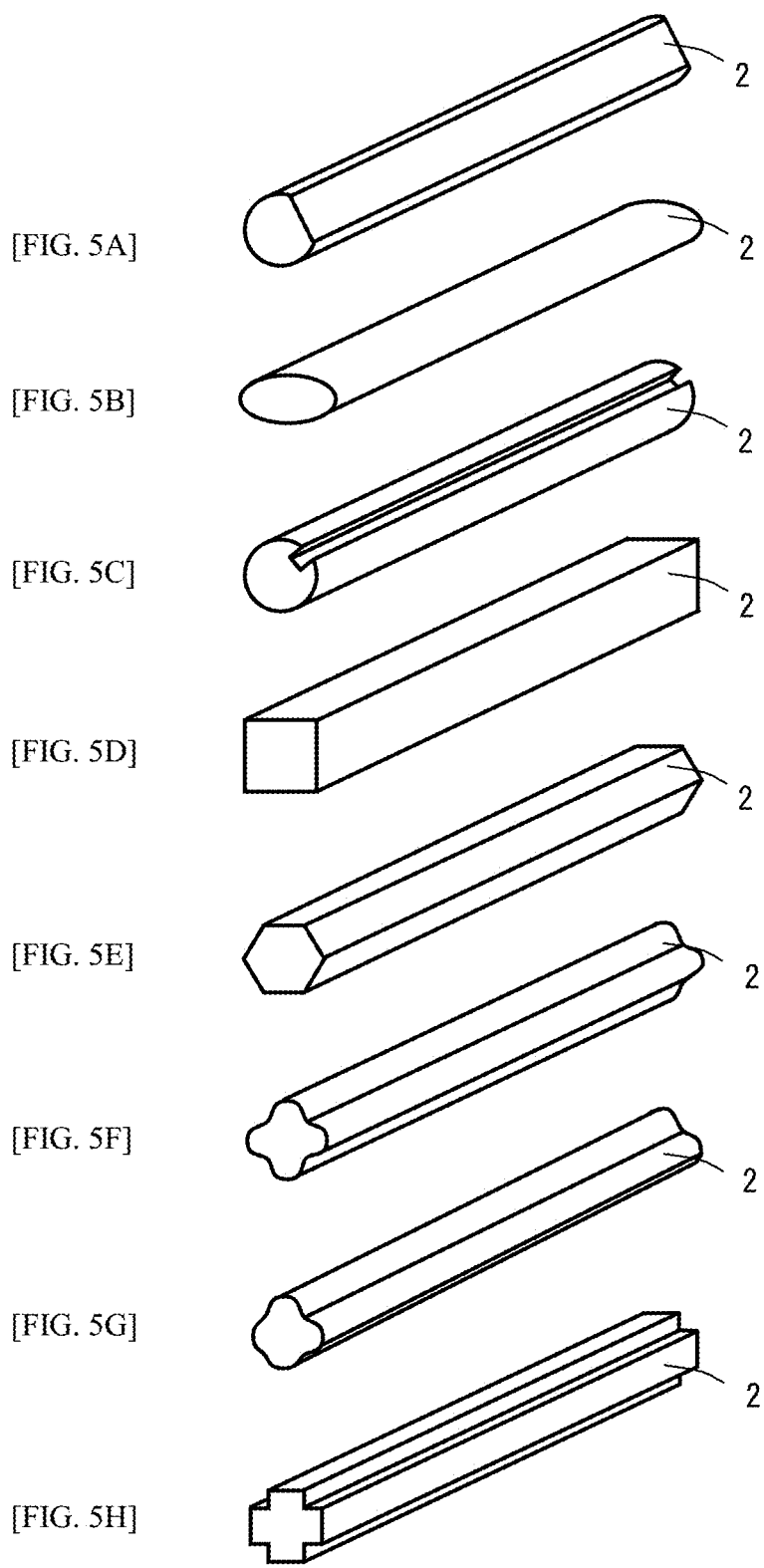

[FIG. 6A]
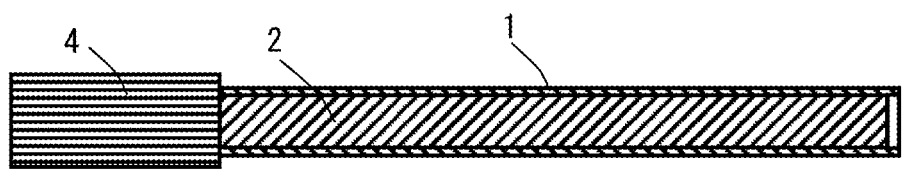
[FIG. 6B]
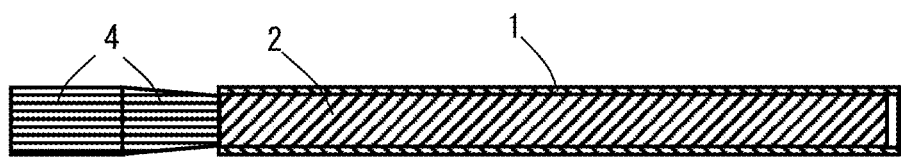
[FIG. 6C]
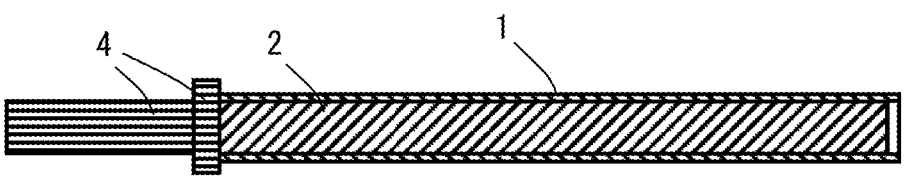
[FIG. 6D]
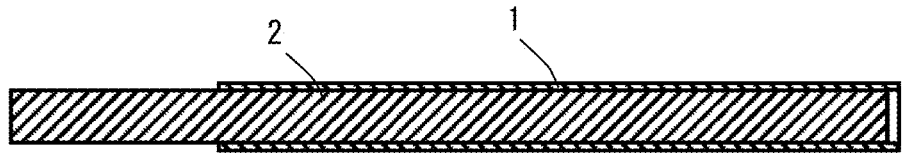

[FIG. 7]
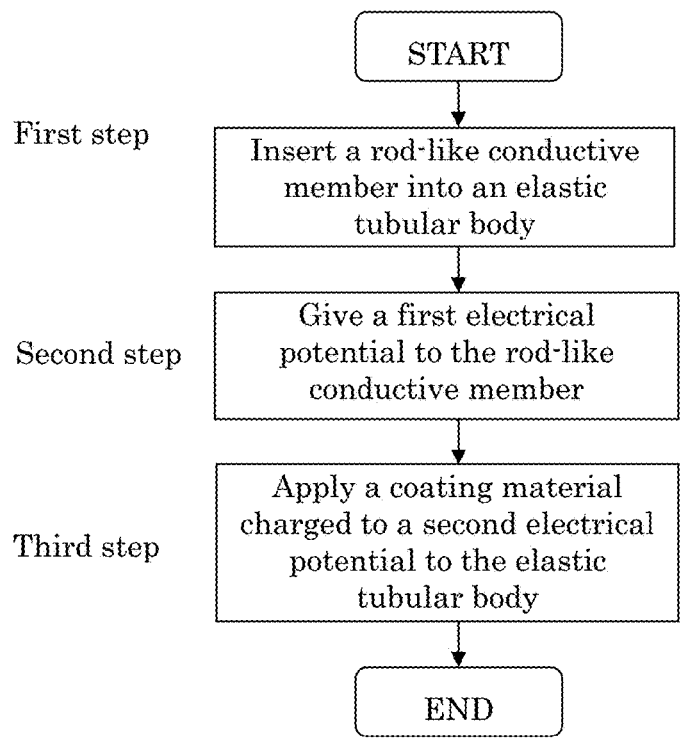
[FIG. 8]
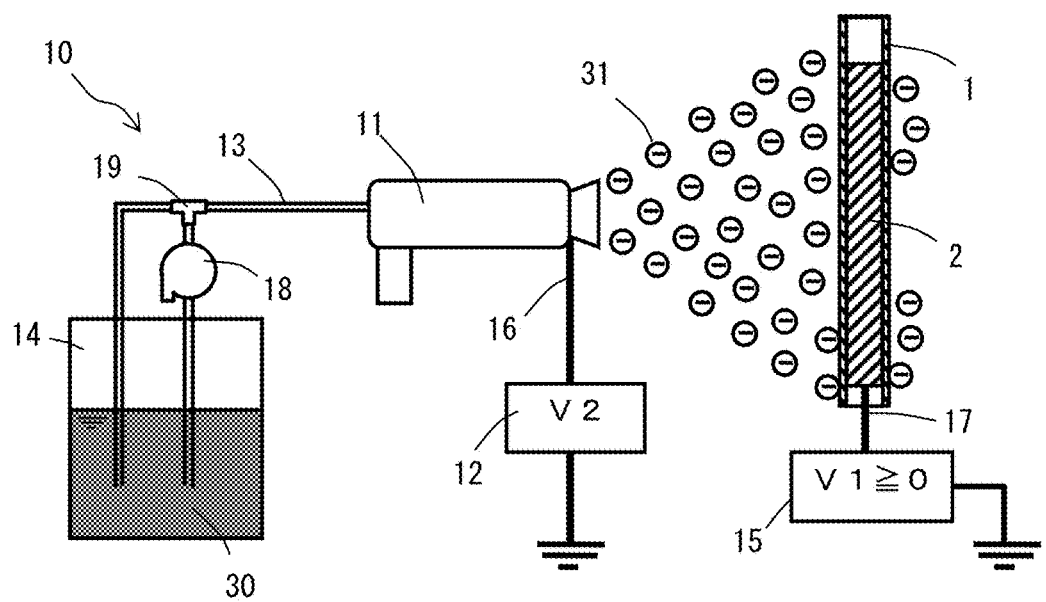

METHOD FOR MANUFACTURING ELASTIC TUBULAR BODY

TECHNICAL FIELD

The present invention relates to a method for manufacturing an elastic tubular body suitable for a medical catheter, for example.

BACKGROUND ART

An outer surface of a medical elastic tubular body such as catheter is applied with a coating material for smooth insertion into a blood vessel and for protecting the elastic tubular body itself.

Ordinary coating application methods include dip coating, brushing, non-electrostatic spray coating, and electrostatic spray coating. Performances of coating methods can be compared and evaluated with various indexes such as application efficiency (dose to a coating-required part (g)/actual application amount (g)), application speed, coating film uniformity, amount of generated waste, and cost.

Dip coating is a method where a coating object is immersed for a predetermined period in a tank stored with a coating liquid. Dip coating is often used since a coating material can be uniformly applied to the coating object, but its production capacity is limited due to its batch style and an application speed affecting a film thickness. In addition, in dip coating, a coating liquid must be stored in a tank, and, when a period of use of the coating liquid expires, a large amount of the coating liquid must be discarded at a time, thus a cost increases.

Brushing is a method for directly applying a coating liquid to a coating object using a brush or a piece of sponge. Through brushing, a coating liquid can be applied to a desired. part, but it is difficult to create a uniform coating film, and, in addition, its productivity is low.

Non-electrostatic spray coating is a method for spraying, onto a coating object, an atomized coating liquid using a spray gun. Through non-electrostatic spray coating, a coating liquid can be applied to a desired part at a desired film thickness, and its productivity is higher, compared with dip coating and brushing. However, in non-electrostatic spray coating, its application efficiency is in principle relatively low, and only a coating surface facing an application direction can be coated. So, to uniformly apply a coating liquid in a circumferential direction, a plurality of spray guns has to be disposed, or a coating object has to be rotated while applying a coating liquid, thus a complicated device structure is required.

Electrostatic spray coating is a method where, while a voltage is given to a coating liquid for charging, the coating liquid is atomized, and then a coating object is grounded or its electrical potential is made opposite to an electrical potential of the coating liquid to spray the charged coating liquid onto the coating object using an electrostatic spray gun. The charged coating material applies to the coating object by an electrostatic force. Electrostatic spray coating is known its relatively higher application efficiency, thus high productivity, For example, Patent Document 1 describes a method for performing electrostatic spray coating onto a metallic stent provided on a balloon formed at an end of a catheter. The catheter has a conductor attached to its outer surface so as to make an electric connection between the stent and the conductor. An electric charge is given to the conductor by grounding the conductor or by connecting the conductor to an electric charge opposite to an electric charge of coating particles, and the charged coating particles are electrically attracted and applied to the stent.

Patent Document 2 describes a method for performing coating, using electrostatic spray coating, onto an outer surface of a lumen of a stent press-fitted onto a balloon catheter. With this method, an electric conductive wire is passed into a lumen of a stent-balloon assembly, and an electric charge is given to the electric conductive wire. In addition, the stent is grounded, or given an electrical potential with an electric charge opposite to an electric charge of the electric conductive wire Patent Documents 1 and 2 both describe methods applicable when a coating object has a conductivity. When a coating object is an insulator, to allow an electric charge to easily move, an electro-conductive treatment liquid is normally coated to the coating object beforehand, and then a coating material is applied. However, since such a pretreatment requires time and cost, a method shown below has been developed.

Patent Document 3 describes a method, with an electrostatic spray coating device including a coater for spraying a coating material to a surface of a coating object having a higher electric resistance value, and a high-voltage generator for giving, to the coater, a high voltage having an electrical potential on a polarity, for supporting the coating object with a support made of an insulator having a higher electric resistance value, and, on a back of a side facing the coater, with the coating object interposed, disposing, in proximity to the coating object, a ground electrode having a ground electrical potential.

Patent Document 4 describes a method, using a coating material having a conductivity or a coating material in which an electrostatic aid is added to lower a resistance value, for mounting a coating object on a stand, a jig, or a conveyor having a conductivity to perform coating from a contact position between the coaling object and the stand, the jig, or the conveyor having a conductivity.

CITATION LIST

Patent Literature

PATENT LITERATURE 1
  Japanese Unexamined Patent Application Publication No. 2007-534362
PATENT LITERATURE 2
  Japanese Unexamined Patent Application Publication No. 2008-534155
PATENT LITERATURE 3
  Japanese Unexamined Patent Application Publication No. S60-38049
PATIENT LITERATURE 4
  Japanese Unexamined Patent Application Publication No. 2000-153217

SUMMARY OF INVENTION

Technical Problem

However, both the above described Patent Documents 1 and 2 describe coating methods when a coating object has a conductivity. On the other hand, with the methods described in Patent Documents 3 and 4, it has actually been difficult to properly control a flow of a coating material, thus it has been difficult to uniformly apply the coating material to a tubular body in a circumferential direction. In view of the above described problems, the present invention has an object to provide a method for manufacturing an elastic tubular body uniformly applied a coating material.

Solution To Problem

To solve the above described problems, the inventors of the present invention have performed various tests where a columnar conductive member is inserted into an elastic tubular body, i.e. coating object, a predetermined electrical potential is given to this columnar conductive member, an electrical potential having a positive or negative polarity opposite to a polarity of this applied electrical potential is given to a coating material, the coating material is atomized, and the coating material is applied to the elastic tubular body by an electrostatic force. As a result, the inventors of the present invention have discovered that, in such electrostatic spray coating, due to an incomplete mutual contact between the elastic tubular body and the columnar conductive member disposed inside the elastic tubular body, an electric charge (electron) given to the coating material are not well delivered toward the columnar conductive member, thus a surface of the elastic tubular body has been charged up by the charged coating material. Once the surface of the elastic tubular body has been charged up, a newly supplied charged coating material receives a repulsive force from the charged coating material already applied to the elastic tubular body, thus the newly supplied charged coating material does not uniformly apply to the elastic tubular body.

To allow an elastic tubular body and a columnar conductive member to securely contact, the inventors of the present invention have thought that simply increasing a diameter of the columnar conductive member is a possible idea However, a columnar conductive member having an increased diameter can possibly damage an elastic tubular body when inserting the columnar conductive member into the elastic tubular body. In addition, as a result of plastic deformation in the elastic tubular body, the coated elastic tubular body might not have a desired diameter.

Further, the inventors of the present invention have found that, through various tests, an electric charge can effectively move for secure delivery from a coating material to a columnar conductive member by, rather than allowing an elastic tubular body to gently and uniformly contact around the columnar conductive member, allowing the elastic tubular body to relatively strongly and securely, even if partially, contact around the columnar conductive member. In addition, as a method for preventing a load onto an elastic tubular body into which a conductive member will be inserted from being increased, and, at the same time, securely delivering an electric charge, the inventors of the present invention have finally thought and applied a deformed cross-sectional shape for the conductive member, rather than a circular cross-sectional shape.

The method for manufacturing an elastic tubular body of the present invention which is able to achieve the above object comprises a first step of inserting a rod-like conductive member into an elastic tubular body, a second step of giving a first electrical potential to the rod-like conductive member, and a third step of applying a coating material charged to a second electrical potential to the elastic tubular body, wherein the rod-like conductive member has a deformed cross-sectional shape in a direction vertical to an axial direction. In the method for manufacturing the elastic tubular body, according to the present invention, since the rod-like conductive member has the deformed cross-sectional shape in the direction vertical to the axial direction, the elastic tubular body inserted with the rod-like conductive member deforms along the shape of the rod-like conductive member such that the elastic tubular body is in surface contact with the rod-like conductive member, thus a mutual contact part is securely created. In addition, although the coating material charged to the second electrical potential applies to the elastic tubular body by an electrostatic force, the first electrical potential given to the rod-like conductive member causes an electric charge applied to a surface of the elastic tubular body to move to the rod-like conductive member through the contact part between the elastic tubular body and the rod-like conductive member, thus an electric charge accumulated on the surface of the elastic tubular body can be removed. This can prevent a coating material from being not applied to an outer surface of the elastic tubular body due to that an electric charge accumulated on the surface of the elastic tubular body and an electric charge of a coating material to be newly applied to the elastic tubular body electrically repel. Accordingly, a coating material is prevented from being non-uniformly applied to the outer surface of the elastic tubular body in a circumferential direction.

With the method for manufacturing the elastic tubular body according to present invention, it is preferred that a length of a minimum route around the deformed cross-sectional shape is greater than that of an inner circumference of the elastic tubular body. Therefore, the elastic tubular body and the rod-like conductive member can easily contact with each other.

With the method for manufacturing the elastic tubular body according to the present invention, it is preferred that an outer circumference of the deformed cross-sectional shape is present at an inner position of the minimum route around the deformed cross-sectional shape and does not contact with the minimum route in at least a partial section. in at least the partial section of the outer circumference of the deformed cross-sectional shape, since the elastic tubular body and the rod-like conductive member do not contact with each other, the elastic tubular body is prevented from being damaged due to that the elastic tubular body is inserted with the rod-like conductive member and expanded exceeding a limit in a radial direction.

With the method for manufacturing the elastic tubular body according to the present invention, it is preferred that the outer circumference of the rod-like conductive member has at least two of the sections hereinafter referred to as first sections where the outer circumference of the deformed cross-sectional shape is present at an inner position of the minimum route around the deformed cross-sectional shape and does not contact with the minimum route, and the elastic tubular body and the rod-like conductive member contact with each other in some part (hereinafter referred to as second section) other than the first sections. When a plurality of the first sections where the outer circumference of the deformed cross-sectional shape is present at the inner position of the minimum route around the deformed cross-sectional shape and does not contact with the minimum route presents, a plurality of the second sections where the elastic tubular body and the rod-like conductive member contact with each other can present. When a plurality of the contact parts presents between the elastic tubular body and the rod-like conductive member, an electric charge transfer from the elastic tubular body to the rod-like conductive member occurs at the plurality of the contact parts, thus, compared with a case of a single contact part, the outer surface of the elastic tubular body is less likely to be accumulated with an electric charge. Therefore, a coating material is prevented from being non-uniformly applied to the outer surface of the elastic tubular body in the circumferential direction, due to that an electric charge accumulated on the outer surface of the elastic tubular body and an electric charge of a coating material to be newly applied to the elastic tubular body electrically repel.

With the method for manufacturing the elastic tubular body according to the present invention, it is preferred that a relationship between a total length L1 of the sections (the first sections) where the outer circumference of the deformed cross-sectional shape is present at an inner position of the minimum route around the deformed cross-sectional shape and does not contact with the minimum route, and a total length L2 of other sections (the second sections) where the elastic tubular body and the rod-like conductive member contact with each other satisfies the following inequality: 0 <L1<L2, When the total length L2 of the second sections where the elastic tubular body and the rod-like conductive member contact with each other is greater than the total length L1 of the first sections, i.e. the more a number of the contact parts between the elastic tubular body and the rod-like conductive member increases, the more an electric charge transfer from the elastic tubular body to the rod-like conductive member occurs in a plurality of the contact parts, thus the less an electric charge accumulates on the outer surface of the elastic tubular body, compared with a case of a single contact part. As a result, an electric charge accumulated on the outer surface of the elastic tubular body and an electric charge of a coating material to be newly applied to the elastic tubular body are less likely to repel, thus, a coating material is prevented from being non-uniformly applied to the outer surface of the elastic tubular body in the circumferential direction.

With the method for manufacturing the elastic tubular body according to the present invention, it is preferred that the deformed cross-sectional shape is uniform in an axial direction of the elastic tubular body. When the elastic tubular body and a rod-like conductive member uniformly contact with each other in the axial direction of the elastic tubular body, a deviation in an amount of an electric charge moving, per a contact part, from the elastic tubular body to the rod-like conductive member is less likely to occur, thus a coating material is prevented from being non-uniformly applied to the outer surface of the elastic tubular body in the axial direction, due to that an electric charge accumulated on the outer surface of the elastic tubular body and an electric charge of a coating material to be newly applied to the elastic tubular body electrically repel.

With the method for manufacturing the elastic tubular body according to t e present invention, it is preferred that the rod-like conductive member has a section where an area of the deformed cross-sectional shape increases in the axial direction. The larger the area of the deformed cross-sectional shape, the smaller an electric resistance in the rod-like conductive member. Therefore, when the rod-like conductive member has the section where the area of the deformed cross-sectional shape increases in the axial direction, a current can easily flow to the rod-like conductive member in the section. Therefore, the outer surface of the elastic tubular body is less likely to be accumulated with an electric charge.

With the method for manufacturing the elastic tubular body according to the present invention, it is preferred that the elastic tubular body and the rod-like conductive member contact with each other at respective sections $A_1, A_2, \ldots, A_M$ that are derived by dividing the inner circumference of the elastic tubular body into M-equal parts, wherein the $M \geq 2$. In this case, the rod-like conductive member and the elastic tubular body contact with each other in the circumferential direction at a constant interval. Therefore, in the circumferential direction of the elastic tubular body, a deviation in an amount of an electric charge moving from the elastic tubular body to the rod-like conductive member is less likely to occur, thus a coating material is prevented from being non-uniformly applied to the outer surface of the elastic tubular body in the circumferential direction.

With the method for manufacturing the elastic tubular body according to the present invention, it is preferred that the elastic tubular body and the rod-like conductive member contact with each other at an equal interval in a circumferential direction of the rod-like conductive member, Therefore, a deviation in an amount of an electric charge moving, per the contact part, from the elastic tubular body to the rod-like conductive member is further less likely to occur, thus a coating material is prevented from being non-uniformly applied to the outer surface of the elastic tubular body in the circumferential direction.

With the method for manufacturing the elastic tubular body according to the present invention, it is preferred that local maximum parts of a radius of the rod-like conductive member are arranged at an equal interval in the circumferential direction of the rod-like conductive member. Therefore, the rod-like conductive member can easily contact with the elastic tubular body at the equal interval in the circumferential direction. Accordingly, a deviation in an amount of an electric charge moving, per the contact part, from the elastic tubular body to the rod-like conductive member can be prevented from occurring.

With the method for manufacturing the elastic tubular body according to the present invention, it is preferred that the rod-like conductive member has at least three of the local maximum parts of the radius, and an outer diameter of a virtual circle through the three of the local maximum parts of the radius is larger than an inner diameter of the elastic tubular body. Therefore, when the rod-like conductive member is inserted into the elastic tubular body, the inner circumference of the elastic tubular body deforms along the cross-sectional shape of the rod-like conductive member so that the elastic tubular body and the rod-like conductive member can securely contact with each other.

With the method for manufacturing the elastic tubular body according to the present invention, it is preferred that an outer diameter of a handle provided in the rod-like conductive member is larger than the outer diameter of the virtual circle. A part of the handle with the outer diameter larger than the outer diameter of the virtual circle will not be inserted into the elastic tubular body in the first step. Therefore, the handle can seal an end of the elastic tubular body to prevent a coating material from being entered into an inner surface of the elastic tubular body, and, in addition, a relative position between the elastic tubular body and a rod-like conductive member can be determined.

With the method for manufacturing the elastic tubular body according to present invention, it is preferred that the rod-like conductive member has a higher electrical conductivity than the elastic tubular body. Therefore, an electric charge accumulated on the outer surface of the elastic tubular body can be easily removal A rod-like conductive member of the present invention for use in the method for manufacturing the elastic tubular body described above can effectively reduce non-uniform application of a coating material to the outer surface of the elastic tubular body in the circumferential direction.

Advantageous Effects of Invention

The method for manufacturing an elastic tubular body of the present invention comprises a first step of inserting a rod-like conductive member into an elastic tubular body, a second step of giving a first electrical potential to the rod-like conductive member, and a third step of applying a coating material charged to a second electrical potential to the elastic tubular body, wherein the rod-like conductive member has a deformed cross-sectional shape in a direction vertical to an axial direction. In the method for manufacturing the elastic tubular body, according to the present invention, since the rod-like conductive member has the deformed cross-sectional shape in the direction vertical to the axial direction, the elastic tubular body inserted with the rod-like conductive member deforms along the shape of the rod-like conductive member such that the elastic tubular body is in surface contact with the rod-like conductive member, thus a mutual contact part is securely created. In addition, although the coating material charged to the second electrical potential applies to the elastic tubular body by an electrostatic force, the first electrical potential given to the rod-like conductive member causes an electric charge applied to an outer surface of the elastic tubular body to move to the rod-like conductive member through the contact part between the elastic tubular body and the rod-like conductive member, thus an electric charge accumulated on the outer surface of the elastic tubular body can be removed. This can prevent a coating material from being not applied to the outer surface of the elastic tubular body due to that an electric charge accumulated on the outer surface of the elastic tubular body and an electric charge of a coating material to be newly applied to the elastic tubular body electrically repel. Accordingly, a coating material is prevented from being non-uniformly applied to the outer surface of the elastic tubular body in a circumferential direction.

BRIEF DESCRIPTION OF THE DRAWINGS

FIGS. 1A to 1F are cross-sectional views of elastic tubular bodies according to an embodiment of the present invention, where FIG. 1A is a cross-sectional view along an axial direction of an elastic tubular body having a single tube structure, FIG. 1B is cross-sectional view along a line I-I of the elastic tubular body shown in FIG. 1A. FIG. 1C is a cross-sectional view along an axial direction of an elastic tubular body having a multiple tube structure, FIG. 1D is cross-sectional view along a line I-I of the elastic tubular body shown in FIG. 1C, FIG. 1E is a cross-sectional view along an axial direction of an elastic tubular body having a combination structure of a single tube and a multiple tube, FIG. 1F is cross-sectional view along a line I-I of the elastic tubular body shown in FIG. 1E.

FIG. 2 is a cross-sectional view in a direction vertical to an axial direction of a rod-like conductive member according to the embodiment of the present invention, FIG. 3 is a side view of the elastic tubular body and the rod-like conductive member according to the embodiment of the present invention FIG. 4 is a view showing a size relationship between cross sections in the direction vertical to the axial direction of the elastic tubular body and the rod-like conductive member according to the embodiment of the present invention.

FIGS. 5A to 5H are perspective views of rod-like conductive members according to the embodiment of the present invention, where FIG. 5A shows a cross-sectional shape in a direction vertical to an axial direction of a rod-like conductive member is a cut circular shape where a circle is partially cut in straight, FIG. 5B shows a cross-sectional shape in the direction vertical to the axial direction of a rod-like conductive member is an elliptical shape, FIG. 5C shows a cross-sectional shape in the direction vertical to the axial direction of a rod-like conductive member is a shape partially formed with a recess on a circular surface, FIG. 5D shows a cross-sectional shape in the direction vertical to the axial direction of a rod-like conductive member is a square shape, FIG. 5E shows a cross-sectional shape in the direction vertical to the axial direction of a rod-like conductive member is a hexagonal shape, FIG. 5F shows a cross-sectional shape in the direction vertical to the axial direction of a rod-like conductive member is a wavy shape having a regular cycle and a regular amplitude, FIG. 5G shows a cross-sectional shape in the direction vertical to the axial direction of a rod-like conductive member is a wavy shape where a cycle and an amplitude are irregular in a circumferential direction, FIG. 5H shows a cross-sectional shape in the direction vertical to the axial direction of a rod-like conductive member is a cruciform.

FIGS. 6A to 6D are cross-sectional views in the axial direction of tubular elastic bodies when the elastic tubular bodies are each inserted with a rod-like conductive member according to the embodiment of the present invention, where FIG. 6A shows a columnar handle, FIG. 6B shows a tapered handle, FIG. 6C shows a flanged handle, FIG. 6D shows a rod-like conductive member without a handle.

FIG. 7 is a flowchart of a method for manufacturing an elastic tubular body according to the embodiment of the present invention.

FIG. 8 is a view showing a configuration of an electrostatic spray coating device according to the embodiment of the present invention.

DESCRIPTION OF EMBODIMENTS

The present invention will be specifically explained below based on the following embodiments, however, the present invention is not restricted by the embodiments described below of course, and can be certainly put into practice after appropriate modifications within in a range meeting the gist of the above and the below. all of which are included in the technical scope of the present invention. In the drawings, hatching, a reference sign for a member may be omitted for convenience, and in such a case, the description and other drawings should be referred to. In addition, sizes of various members in the drawings may differ from the actual sizes thereof, since priority is given to understanding the features of the present invention.

The method for manufacturing an elastic tubular body of the present invention comprises a first step of inserting a rod-like conductive member into an elastic tubular body, a second step of giving a first electrical potential to the rod-like conductive member, and a third step of applying a coating material charged to a second electrical potential to the elastic tubular body, wherein the rod-like conductive member has a deformed cross-sectional shape in a direction vertical to an axial direction. In the method for manufacturing the elastic tubular body, according to the present invention, since the rod-like conductive member has the deformed cross-sectional shape in the direction vertical to the axial direction, the elastic tubular body inserted with the rod-like conductive member deforms along the shape of the rod-like conductive member such that the elastic tubular body is in surface contact with the rod-like conductive member, thus a mutual contact part is securely created. In addition, although the coating material charged to the second electrical potential applies to the elastic tubular body by an electrostatic force, the first electrical potential given to the rod-like conductive member causes an electric charge applied to an outer surface of the elastic tubular body to move to the rod-like conductive member through the contact part between the elastic tubular body and the rod-like conductive member, thus an electric charge accumulated on the outer surface of the elastic tubular body can be removed. This can prevent a coating material from being not applied to the outer surface of the elastic tubular body due to that an electric charge accumulated on the outer surface of the elastic tubular body and an electric charge of a coating material to be newly applied to the elastic tubular body electrically repel. Accordingly, a coating material is prevented from being non-uniformly applied to the outer surface of the elastic tubular body in a circumferential direction.

In the method for manufacturing the elastic tubular body according to the present invention, the elastic tubular body is a tubular member formed of a material having elasticity. The elastic tubular body is, for example, a resin tube, and is used for a catheter, a resin stent, a drainage tube, and other similar equipment in a medical field.

A shape of the elastic tubular body is not particularly limited, as long as the shape is tubular. FIGS. 1A to 1F are cross-sectional views of elastic tubular bodies 1 according to an embodiment of the present invention, where FIG. 1A is a cross-sectional view along the axial direction of an elastic tubular body having a single tube structure, FIG. 1C is a cross-sectional view along the axial direction of an elastic tubular body having a multiple tube structure, and FIG. 1E is a cross-sectional view along the axial direction of an elastic tubular body having a combination structure of a single tube and a multiple tube. In addition, FIGS. 1B, ID, and 1F respectively are cross-sectional views along a line I-I of the tubular elastic bodies 1 shown in FIGS. 1A, 1C, and 1E. For example, as shown in FIGS. 1A and 1B, the elastic tubular body 1 may have a single tube structure. In addition, the elastic tubular body 1 may have, as shown in FIGS. 1C and 1D, a multiple tube structure formed of a plurality of concentric tubes having different diameters. With such the elastic tubular body 1 having a multiple tube structure, gas or liquid can be filled in a space between different tubes. Further, an elastic tubular body 1 may be, as shown in FIGS. 1E and 1F, combined with a single tube structure and a multiple tube structure. At a multiple tube part 1c of a single tube part 1a side as shown in FIG. 1E, a balloon part 1d that can inflate or deflate may be formed. For example, by inserting the elastic tubular body 1 having such the balloon section 1d into a blood vessel, and inflating the balloon part 1d at a desired position, a stenotic part in the blood vessel can be expanded. The elastic tubular body 1 may have different outer diameters at positions in the axial direction due to such the balloon part 1d, a part overlapped with another tube.

It is preferred that a wall thickness of the elastic tubular body is constant in the axial direction. Therefore, the elastic tubular body can easily be manufactured. The wall thickness of the elastic tubular body may not be constant in the axial direction, and an inner diameter or an outer diameter of the elastic tubular body may differ at a position in the axial direction. With the method according to the present invention, a coating material can he applied to even the elastic tubular body having a different outer diameter or a different inner diameter at the position in the axial direction.

A material of the elastic tubular body is not limited, as long as the material has elasticity, and may be a conductor or an insulator. Available insulation resins for an insulator include, for example, one or more of nylon, polyurethane, polyethylene, polypropylene, polycarbonate, polyvinyl chloride, polyvinylidene fluoride, silicone, polytetrafluoroethylene, tetrafluoroethylene-perfluoro alkyl vinyl ether copolymer, and tetrafluoroethylene-hexafluoropropylene copolymer.

The rod-like conductive member is a rod-like shaped member having at least a surface formed of a conductive material, and is inserted into a lumen of the elastic tubular body. The rod-like conductive member has a deformed cross-sectional shape in the direction vertical to the axial direction. Here, the deformed cross-sectional shape means a non-circular cross-sectional shape.

It is preferred that a length of a minimum route around the deformed cross-sectional shape, in the direction vertical to the axial direction, of the rod-like conductive member is greater than that of an inner circumference of the elastic tubular body. Therefore, the elastic tubular body and the rod-like conductive member can easily contact with each other Here, the minimum route is a route that goes around the rod-like conductive member with a minimum distance, and is, for example, a virtual route formed by winding a string around the rod-like conductive member in a circumferential direction. The inner circumference of the elastic tubular body at this time means an inner circumference of the elastic tubular body when no rod-like conductive member is inserted into the elastic tubular body.

FIG. 2 is a cross-sectional view, in the direction vertical to the axial direction, of a rod-like conductive member 2 according to the embodiment of the present invention. As shown in FIG. 2, it is preferred that an outer circumference 2a of the deformed cross-sectional shape, in the direction vertical to the axial direction, of the rod-like conductive member 2 is present at an inner position of the minimum route 2b around the deformed cross-sectional shape, in the direction vertical to the axial direction, of the rod-like conductive member 2 and the outer circumference 2a and the minimum route 2b do not contact with each other in at least a partial section 3a. In at least the partial section of the outer circumference 2a of the deformed cross-sectional shape, since the elastic tubular body 1 and the rod-like conductive member 2 do not contact with each other, the elastic tubular body 1 is prevented from being damaged due to that the elastic tubular body 1 is inserted with the rod-like conductive member 2 and expanded exceeding a limit in a radial direction.

It is preferred that the rod-like conductive member 2 has, for example, at least two of the sections (first sections 3a), and the elastic tubular body 1 and the rod-like conductive member 2 contact with each other in a second section 3b other than the first sections. When a plurality of the first sections 3a where the outer circumference of the deformed cross-sectional shape is present at the inner position of the minimum route 2b around the deformed cross-sectional shape and the outer circumference 2a and the minimum route 2b do not contact with each other presents, a plurality of the second sections 3b where the elastic tubular body 1 and the rod-like conductive member 2 contact with each other can present. When a plurality of contact parts presents between the elastic tubular body 1 and the rod-like conductive member 2, an electric charge transfer from the elastic tubular body 1 to the rod-like conductive member 2 occurs at the plurality of the contact parts, thus, compared with a case of a single contact part, the outer surface of the elastic tubular body 1 is less likely to be accumulated with an electric charge, and non-uniformity in accumulating an electric charge can easily be reduced. As a result, an electric charge accumulated on the outer surface of the elastic tubular body 2 and an electric charge of a coating material to be newly applied to the elastic tubular body 1 are less likely to repel, thus, a coating material is prevented from being non-uniformly applied to the outer surface of the elastic tubular body 1 in the circumferential direction.

It is preferred that a relationship between a total length L1 of the first sections where the outer circumference of the deformed cross-sectional shape is present at the inner position of the minimum route around the deformed cross-sectional shape of the rod-like conductive member and the outer circumference of the deformed cross-sectional shape and the minimum route do not contact with each other, and a total length L2 of the second sections where the elastic tubular body and the rod-like conductive member contact with each other is set so as to satisfy the following inequality: 0<L<L2. When a number of contact parts between the elastic tubular body and the rod-like conductive member increases, an electric charge accumulated on the outer surface of the elastic tubular body and an electric charge of a coating material to be newly applied to the elastic tubular body are less likely to repel, thus, a coating material is prevented from being non-uniformly applied to the outer surface of the elastic tubular body in the circumferential direction.

It is preferred that the elastic tubular body and the rod-like conductive member contact with each other at respective sections $A_1, A_2, \ldots, A_M$ that are derived by dividing the inner circumference of the elastic tubular body into M-equal parts, wherein the M≥2. In this case, the rod-like conductive member and the elastic tubular body contact with each other in the circumferential direction at a constant interval. Therefore, in the circumferential direction of the elastic tubular body, a deviation in an amount of an electric charge moving from the elastic tubular body to the rod-like conductive member is less likely to occur, thus a coating material is prevented from being non-uniformly applied to the outer surface of the elastic tubular body in the circumferential direction.

To increase a number of contact parts between the rod-like conductive member and the elastic tubular body, the number M for equal-dividing the elastic tubular body in the circumferential direction is preferably 3 or larger, more preferably 4 or larger. On the other hand, an excessive number of contact parts between the rod-like conductive member and the elastic tubular body reduces a part where the rod-like conductive member and the elastic tubular body do not contact with each other, thus reduces an allowance for when the rod-like conductive member is inserted into and expanded the elastic tubular body. As a result, the elastic tubular body could be broken. Therefore, the number M for equal-dividing the elastic tubular body in the circumferential direction is preferably 10 or smaller, more preferably 9 or smaller, further preferably 8 or smaller.

It is preferred that a section where the rod-like conductive member and the elastic tubular body do not contact with each other is present in the section $A_M$ of the elastic tubular body. That is, it is preferred that both a section where the rod-like conductive member and the elastic tubular body contact with each other and a section where the rod-like conductive member and the elastic tubular body do not contact with each other are present in the section $A_M$ of the elastic tubular body. Such the section where the rod-like conductive member and the elastic tubular body do not contact with each other in the section $A_M$, functions as an allowance that prevents the elastic tubular body from being expanded in the radial direction exceeding a limit by the rod-like conductive member, thus prevents the elastic tubular body from being damaged, when the rod-like conductive member is inserted into the elastic tubular body.

FIG. 3 is aside view of the elastic tubular body 1 and the rod-like conductive member 2 according to the embodiment of the present invention. Fan shaped sections $A_1, A_2, A_3,$ and $A_4$ are formed by dividing the inner circumference of the elastic tubular body 1 into four equal parts, where the elastic tubular body 1 and the rod-like conductive member 2 respectively contact with each other in the sections $A_1, A_2, A_3,$ and $A_4$ of the elastic tubular body 1. Therefore a deviation in an amount of an electric charge moving from the elastic tubular body to the rod-like conductive member is less likely to occur in the circumferential direction of the elastic tubular body, thus a coating material is prevented from being non-uniformly applied to the outer surface of the elastic tubular body in the circumferential direction.

As shown in FIG. 3, it is preferred that the elastic tubular body 1 and the rod-like conductive member 2 contact with each other at an equal interval in the circumferential direction of the rod-like conductive member 2. Therefore, a deviation in an amount of an electric charge moving, per a contact parts, from the elastic tubular body to the rod-like conductive member is further less likely to occur, thus a coating material is prevented from being non-uniformly applied to the outer surface of the elastic tubular body, in the circumferential direction.

FIG. 4 is a view showing a size relationship between cross sections, in a direction vertical to the axial direction, of the elastic tubular body 1 and the rod-like conductive member 2 according to the embodiment of the present invention. As shown in FIG. 4, it is preferred that local maximum parts 2c of a radius of the rod-like conductive member 2 are arranged at an equal interval in the circumferential direction of the rod-like conductive member 2. Therefore, the rod-like conductive member 2 can easily contact with the elastic tubular body 1 at the equal interval in the circumferential direction. Accordingly, a deviation in an amount of an electric charge moving, per the contact part, from the elastic tubular body 1 to the rod-like conductive member 2 can be prevented from occurring. Here, the local maximum parts 2c of a radius is referred to, when the rod-like conductive member 2 is viewed in across section in the direction vertical to the axial direction, and when a distance from a center of gravity of the rod-like conductive member 2 to the outer circumference 2a is specified to a radius, as a point at which the radius becomes local maximum, and an equal interval means that a difference in a distance between one of the local maximum parts 2c of radius and another adjacent one of the local maximum parts 2c of radius falls within ±15%.

As shown in FIG. 4, it is preferred that the rod-like conductive member 2 has at least three of the local maximum parts 2c of the radius, and an outer diameter of a virtual circle 2d unambiguously determined by passing through the three of the local maximum parts 2c of the radius is larger than an inner diameter le of the elastic tubular body. Therefore, When the rod-like conductive member 2 is inserted into the elastic tubular body 1, the inner circumference of the elastic tubular body 1 deforms along the cross-sectional shape of the rod-like conductive member 2 so that the elastic tubular body 1 and the rod-like conductive member 2 can securely contact with each other. In addition, it is preferred that, when a rod-like conductive member 1 has the three of the local maximum parts 2c of the radius, an outer diameter Rm (Unit: mm) of the virtual circle 2d is within a range obtained by an inequality shown below. In the inequality, R is an inner diameter of the elastic tubular body 1 (Unit: mm), and N is a number of the local maximum parts 2c of the radius of the rod-like conductive member 2 (Unit: number). When the elastic tubular body 1 and the rod-like conductive member 2 have a relationship satisfying the inequality shown below, the rod-like conductive member 2 neither inserts excessively into the elastic tubular body 1 nor expands the elastic tubular body 1 exceeding a limit in a radial direction, thus the elastic tubular body 1 is prevented from being damaged.

$$R \leq R_m \leq R \frac{\pi}{N \sin\left(\frac{\pi}{N}\right)}$$

FIGS. 5A to 5H are perspective views of rod-like conductive members 2 according to the embodiment of the present invention. A cross-sectional shape, in the direction vertical to the axial direction, of the rod-like conductive member 2 may be, for example, a cut circular shape where a circle is partially cut in straight as shown in FIG. 5A, an elliptical shape as shown in FIG. 5B, a shape partially formed with a recess on a circular surface as shown in FIG. 5C (as a shape of a rod-like conductive member 2, a groove is formed in parallel to the axial direction on a surface of a circular column), or a square shape as shown in FIG. 5D. Still further, a cross-sectional shape may be a hexagonal shape as shown in FIG. 5E, a wavy shape having a regular cycle and a regular amplitude as shown in FIG. 5E a wavy shape where a cycle and an amplitude are irregular in the circumferential direction as shown in FIG. 5G, or a cruciform as shown in FIG. 5H. In addition to the above, a deformed cross-sectional shape may be an arc crescent shape) or another shape.

As described above, when the rod-like conductive member 2 has the deformed cross-sectional shape in the direction vertical to the axial direction, the elastic tubular body 1 inserted with the rod-like conductive member 2 deforms along the shape of the rod-like conductive member 2 such that the elastic tubular body 1 is in surface contact with the rod-like conductive member 2, thus a mutual contact part is securely created. In particular, in a case of the rod-like conductive member 2 having a wavy cross-sectional shape in the direction vertical to the axial direction, the elastic tubular body 1 deforms in a relatively gently manner, thus the elastic tubular body 1 can be prevented from being damaged.

It is preferred that the deformed cross-sectional shape of the rod-like conductive member is uniform in the axial direction of the elastic tubular body. When the elastic tubular body and a rod-like conductive member uniformly contact with each other in the axial direction of the elastic tubular body, a deviation in an amount of an electric charge moving, per a contact part, from the elastic tubular body to the rod-like conductive member is less likely to occur, thus a coating material is prevented from being non-uniformly applied to the outer surface of the elastic tubular body in the axial direction, due to that an electric charge accumulated on the outer surface of the elastic tubular body and an electric charge of a coating material to be newly applied to the elastic tubular body electrically repel.

It is preferred that the rod-like conductive member 2 has a section where an area of the deformed cross-sectional shape increases in the axial direction. Since the larger the area of the deformed cross-sectional shape, the smaller an electric resistance in the rod-like conductive member 2, a current can easily flow to the rod-like conductive member 2 in the axial direction. The rod-like conductive member has the section where the area of the deformed cross-sectional shape increases in the axial direction, a current can easily flow to the rod-like conductive member in the section. Therefore, the outer surface of the elastic tubular body is less likely to be accumulated with an electric charge.

FIGS. 6A to 6D are cross-sectional views in the axial direction of tubular elastic bodies 1 when the elastic tubular bodies 1 are each inserted with a rod-like conductive member 2 according to the embodiment of the present invention. It is preferred that a rod-like conductive member 2 is provided with a handle 4 having an outer diameter larger than the outer diameter of the virtual circle 2d. FIG. 6A shows a columnar handle 4, FIG. 6B shows a tapered handle 4, FIG. 6C shows a flanged handle 4. A handle 4 having such an outer diameter can seal an end of the elastic tubular body 1 to prevent a coating material from being entered into a lumen surface of the elastic tubular body 1, and, in addition, a relative position between the elastic tubular body 1 and a rod-like conductive member 2 can be determined. Moreover, as shown in FIG. 6D, the rod-like conductive member 2 may not be provided with a handle 4. The rod-like conductive member 2 without provided with a handle 4 does not require a step for providing a handle in a step of manufacturing the rod-like conductive members 2, compared with a rod-like conductive member 2 provided with a handle 4, thus a time and cost required for manufacturing can be reduced.

It is preferred that the rod-like conductive member has a higher electrical conductivity than the elastic tubular body. Therefore, an electric charge accumulated on the outer surface of the elastic tubular body can easily be removed. A material available for the rod-like conductive member includes, for example, a metallic material such as iron, stainless steel, silver, and copper, and an insulator such as synthetic resin applied with a conductive material on its surface.

With electrostatic spray coating, an electrostatic spray gun is used to apply a coating material to a coating object. Such an electrostatic spray gun atomizes a coating material supplied into the electrostatic spray gun, charges the atomized coating material, and sprays the coating material onto a coating object. Accordingly, the charged coating material applies to the coating object by an electrostatic force. The electrostatic spray gun is connected to a supplying means supplying an application liquid to the electrostatic spray gun from a storage tank storing the application liquid.

Electrostatic spray coating is roughly categorized into liquid coating and powder coating. Liquid coating is a method for applying a solution in which a coating material is diluted with an organic solvent or water to allow a coating material to apply to a coating object through baking or drying. Powder coating is a method for applying atomized coating powders to allow the coating powders to apply to a coating object through baking or other methods. Powder coating does not use an organic solvent, thus can reduce an impact to human health and environment, and, in addition, allows collection and reuse of a coating material that was not applied to a coating object.

Liquid coating does not particularly limit a type of an electrostatic spray gun, and various electrostatic spray guns in styles, for example, air electrostatic style, air-wrap electrostatic style, rotating atomization electrostatic style can be used. The air electrostatic style is a method where a coating liquid is mixed with air to atomize a coating material. The air-wrap electrostatic style is a method where a pressurized coating liquid is wrapped with a low-pressure gas when sprayed from an electrostatic spray gun. The rotating atomization electrostatic style is a method where a coating material discharged from a conical shaped center part is atomized through a centrifugal force.

With liquid coating, an atomized coating material is generally charged with a high-voltage generator. Specifically, a high voltage is given to an electrode of the high-voltage generator to cause a corona discharge to generate ions to charge a coating material. It is preferred that the high-voltage generator is built into an electrostatic spray gun. Therefore, a configuration of an electrostatic spray coating device can be simplified.

In a case of powder coating, a type of an electrostatic spray gun is not particularly limited, but various electrostatic spray guns in styles can be used, for example, corona charging style and frictional charging style. In a case of powder coating, different from liquid coating, atomized powder particles are used as a coating material, thus no diluent such as organic solvent and water is required. The corona charging style uses a corona discharge generally used in an electrostatic spray gun for liquid coating. The frictional charging style is a method where a coating material is charged through a friction inside a gun.

With a corona charging method, in liquid coating and powder coating, a voltage given to a high-voltage generator may be a positive voltage or a negative voltage, but a voltage is preferably −110 kV or larger and +110 kV or smaller, more preferably −100 kV or larger and 0 kV or smaller, further preferably or larger −90 kV and −30 kV or smaller. Therefore, an electrostatic spray gun can cause a corona discharge.

Although a type of a coating material is not particularly limited, various coatings may be used, for example, silicone resin, urethane resin, acrylic resin, fluorine resin, or a mixture of any or all of them.

It is preferred that a rod-like conductive member is connected to an electrical potential adjusting means. To adjust an electrical potential of the elastic tubular body, the electrical potential adjusting means gives a first electrical potential to the rod-like conductive member. it is preferred that the first electrical potential is a ground electrical potential, or an electrical potential having a sign opposite to a sign of an electric charge of a charged coating material. Therefore, the charged coating material discharged from an electrostatic spray gun can be attracted onto the elastic tubular body.

FIG. 7 is a flowchart of a method for manufacturing the elastic tubular body according to the embodiment of the present invention. The method for manufacturing the elastic tubular body of the present invention comprises a first step of inserting a rod-like conductive member into the elastic tubular body, a second step of giving a first electrical potential to the rod-like conductive member, and a third step of applying the coating material charged to a second electrical potential to the elastic tubular body, wherein the rod-like conductive member has a deformed cross-sectional shape in the direction vertical to the axial direction. Each step will now be described herein in detail.

(1) First Step

In the first step, the rod-like member is inserted into the elastic tubular body. Since the rod-like conductive member has the deformed cross-sectional shape, in the direction vertical to the axial direction, of the elastic tubular body inserted with the rod-like conductive member deforms along the shape of the rod-like conductive member such that the elastic tubular body is in surface contact with the rod-like conductive member, thus a mutual contact part is securely created.

(2) Second Step

In the second step, a first electrical potential is given to the rod-like conductive member. An end of the rod-like conductive member is connected with an electrical potential adjusting means. To adjust an electrical potential of the elastic tubular body, the electrical potential adjusting means gives the first electrical potential to the rod-like conductive member. The first electrical potential is a ground electrical potential, or an electrical potential having a sign opposite to a sign of a second electrical potential of a charged coating material described later. Moreover, the second step may be performed before the first step, or may be performed in parallel to the first step.

(3) Third Step

In the third step, the coating material charged to the second electrical potential is applied to the elastic tubular body. An example when a coating liquid is used is described herein, coating powders can also be used. The coating liquid is stored in a storage tank beforehand. In addition, a high-voltage generator for charging a coating material is connected to an electrode inside an electrostatic spray gun. The high-voltage generator and the electrostatic spray gun is started. A positive or negative second electrical potential is given to the high-voltage generator. Therefore, an electrostatic field is formed between the electrode of the electrostatic spray gun and the elastic tubular body.

The coating liquid stored in the storage tank is supplied from the storage tank to the electrostatic spray gun via a flow passage by a supplying means or other means. The electrostatic spray gun atomizes the coating liquid supplied from the storage tank. The electrode of the electrostatic spray gun given the second electrical potential by the high-voltage generator causes a corona discharge to generate ions to charge the atomized coating material. The charged coating material is attracted by an electrostatic force and applies to the elastic tubular body inserted with the rod-like conductive member given the first electrical potential. The charged coating material discharged from the electrostatic spray gun moves, along the electrostatic field, to not only a side facing a discharge port of the electrostatic spray gun discharging the charged coating material, but also a side opposite to the side facing the discharge port.

In the third step, it is also preferred that a plurality of electrostatic spray guns is used to spray the coating material in a plurality of directions. Or, it is also preferred that the elastic tubular body and the rod-like conductive member are rotated in the circumferential direction to spray a coating material, Therefore, a coating material is less likely to be non-uniformly applied to the elastic tubular body in the circumferential direction.

FIG. 8 is a view showing a configuration of an electrostatic spray coating device 10 used for the method for manufacturing the elastic tubular body 1 according to the embodiment of the present invention. With reference to FIG. 8, the method for manufacturing the elastic tubular body 1 according to the embodiment of the present invention will now be described herein. First, in the first step, insert a rod-like conductive member 2 into a lumen of the elastic tubular body 1. As shown in FIG. 4, the rod-like conductive member 2 has the deformed cross-sectional shape in the direction vertical to the axial direction, Therefore, the elastic tubular body 1 inserted with the rod-like conductive member 2 deforms along the shape of the rod-like conductive member 2 to securely create a part where the elastic tubular body 1 and the rod-like conductive member 2 contact with each other.

Next, in the second step, a first electrical potential V1 is given to the rod-like conductive member 2. An end of the rod-like conductive member 2 is connected to a potential electrical adjusting means 15 via a cable 17. To adjust an electrical potential of the elastic tubular body 1, the electrical potential adjusting means 15 gives the first electrical potential V1 to the rod-like conductive member 2. Moreover, the electrical potential adjusting means 15 is grounded.

Further, in the third step, a coating material 31 charged to a second electrical potential is applied to the elastic tubular body 1. In FIG. 8, a coating liquid 30 is stored in a storage tank 14. The coating liquid 30 is supplied by a supplying means 18 from the storage tank 14, via a valve 19 and a flow passage 13, to an electrostatic spray gun 11. In addition, a high-voltage generator 12 for charging the coating liquid 30 is connected to an inner electrode (not shown) of the electrostatic spray gun 11. The high-voltage generator 12 and the electrostatic spray gun 11 is started. A second electrical potential V2 having a potential with a sign opposite to a sign of the first potential V1 is given to the high-voltage generator 12. Therefore, an electrostatic field is formed between the inner electrode of the electrostatic spray gun 11 and the elastic tubular body 1.

The electrostatic spray gun 11 atomizes the coating liquid 30 supplied from the storage tank 14. The inner electrode of the electrostatic spray gun 11 given the second electrical potential V2 by the high-voltage generator 12 connected to the electrostatic spray gun 11 is allow to cause a corona discharge to generate ions to charge the atomized coating liquid 30. The negative-charged coating material 31 discharges from the electrostatic spray gun 11 toward the elastic tubular body 1 to apply, by an electrostatic force, to the outer surface of the elastic tubular body 1. Since an electric charge accumulated on the outer surface of the elastic tubular body 1 moves, through a contact part between the elastic tubular body 1 and the rod-like conductive member 2, to the rod-like conductive member 2, an electric charge accumulated on the outer surface of the elastic tubular body 1 can be removed. Moreover, in the above described embodiment, although only one electrostatic spray gun is used, a plurality of electrostatic spray guns may also be used to prevent a coating material from being non-uniformly applied.

This application claims the benefit of the priority date of Japanese patent application No. 2014-125753 filed on Jun. 18, 2014. All of the contents of the Japanese patent application No. 2014-125753 filed on Jun. 18, 2014, are incorporated by reference herein.

REFERENCE SIGNS LIST

1: an elastic tubular body
1a: a single tube part
1b, 1c: a multiple tube part
1d: a balloon part
1e: an inner diameter
$A_1, A_2, A_3, A_4$: sections
2: a rod-like conductive member
2a: an outer circumference of a deformed cross-sectional shape
2b: a minimum route around the deformed cross-sectional shape
2c: local Maximum parts of a radius
2d: a virtual circle
3a: a first section
3b: a second section
4: a handle
10: an electrostatic spray coating device
11: an electrostatic spray gun
12: a high-voltage generator
14: a storage tank
15: an electrical potential adjusting means
18: a supplying means
30: a coating liquid
31: a charged coating material

The invention claimed is:

1. A method for manufacturing an elastic tubular body, comprising:
a first step of inserting a rod-like conductive member into an elastic tubular body;
a second step of giving a first electrical potential to the rod-like conductive member; and
a third step of applying a coating material charged to a second electrical potential to the elastic tubular body; wherein
the rod-like conductive member has a deformed cross-sectional shape in a direction vertical to an axial direction, and
a length of a minimum route around the deformed cross-sectional shape is greater than that of an inner circumference of the elastic tubular body.

2. The method according to claim 1, wherein
an outer circumference of the deformed cross-sectional shape is present at an inner position of the minimum route around the deformed cross-sectional shape and does not contact with the minimum route in at least a partial section.

3. The method according to claim 2, wherein
the outer circumference of the rod-like conductive member has at least two of the sections, and
the elastic tubular body and the rod-like conductive member contact with each other in some part other than the sections.

4. The method according to claim 3, wherein
a relationship between a total length L1 of the sections where the outer circumference of the deformed cross-sectional shape is present at an inner position of the minimum route around the deformed cross-sectional shape and does not contact with the minimum route, and a total length L2 of other sections where the elastic tubular body and the rod-like conductive member contact with each other satisfies the following inequality:
$0 < L1 < L2$.

5. The method according to claim 1, wherein
the deformed cross-sectional shape is uniform in an axial direction of the elastic tubular body.

6. The method according to claim 1, wherein
the rod-like conductive member has a section where an area of the deformed cross sectional shape increases in the axial direction.

7. The method according to claim 1, wherein
the elastic tubular body and the rod-like conductive member contact with each other at respective sections $A_1, A_2, \ldots, A_M$ that are derived by dividing the inner circumference of the elastic tubular body into M-equal parts, wherein the M $\geq 2$.

8. The method according to claim 7, wherein
the elastic tubular body and the rod-like conductive member contact with each other at an equal interval in a circumferential direction of the rod-like conductive member.

9. The method according to claim 1, wherein
local maximum parts of a radius of the rod-like conductive member are arranged at an equal interval in the circumferential direction of the rod-like conductive member.

10. The method according to claim 9, wherein
the rod-like conductive member has at least three of the local maximum parts of the radius, and an outer diameter of a virtual circle through the three of the local maximum parts of the radius is larger than an inner diameter of the elastic tubular body.

11. The method according to claim 10, wherein
an outer diameter of a handle provided in the rod-like conductive member is larger than the outer diameter of the virtual circle.

12. The method according to claim 1, wherein
the rod-like conductive member has a higher electrical conductivity than the elastic tubular body.

13. A rod-like conductive member for use in the method according to claim 1.

* * * * *